(12) United States Patent
Dalby et al.

(10) Patent No.: US 11,827,614 B2
(45) Date of Patent: Nov. 28, 2023

(54) SYNTHETIC PATHWAY TO BELZUTIFAN AND CRYSTALLINE PHASES OF SYNTHETIC INTERMEDIATES

(71) Applicants: Merck Sharp & Dohme LLC, Rahway, NJ (US); Werthenstein Biopharma GMBH, Lucerne (CH)

(72) Inventors: Stephen M. Dalby, Springfield Township, NJ (US); Clinton Scott Shultz, Maplewood, NJ (US); Chintal Desai, Flemington, NJ (US); Joshua Lee, Parlin, NJ (US); Zhiwei Chen, Clark, NJ (US); Jungchul Kim, Basking Ridge, NJ (US); Nastaran Salehi Marzijarani, Mahwah, NJ (US); Tao Wang, Cranford, NJ (US); Eric M. Phillips, Jersey City, NJ (US); Patrick Larpent, Luzem (CH); Het P. Patel, Groton, CT (US); Haiheng Guo, Shanghai (CN); Xin Wang, Shanghai (CN); Kangze Dai, Shanghai (CN); Lu Chen, Shanghai (CN); Teng Li, Shanghai (CN); Taotao Lu, Shanghai (CN); Jianjun Duan, Shanghai (CN)

(73) Assignees: Merck Sharp & Dohme LLC, Rahway, NJ (US); Werthenstein Biopharma GMBH, Lucerne (CH)

( * ) Notice: Subject to any disclaimer, the term of this patent is extended or adjusted under 35 U.S.C. 154(b) by 18 days.

(21) Appl. No.: 17/749,452

(22) Filed: May 20, 2022

(65) Prior Publication Data

US 2022/0388974 A1  Dec. 8, 2022

Related U.S. Application Data

(60) Provisional application No. 63/191,356, filed on May 21, 2021.

(51) Int. Cl.
  *C07D 317/72* (2006.01)
  *C07C 317/14* (2006.01)

(52) U.S. Cl.
  CPC .......... *C07D 317/72* (2013.01); *C07C 317/14* (2013.01); *C07B 2200/13* (2013.01)

(58) Field of Classification Search
  CPC .................................................. C07D 317/72

USPC .......................................................... 549/341
See application file for complete search history.

(56) References Cited

U.S. PATENT DOCUMENTS

| 9,969,689 B2 | 5/2018 | Dixon et al. |
| 10,597,366 B2 | 3/2020 | Dixon et al. |
| 2021/0387946 A1 | 12/2021 | Lindemann et al. |
| 2022/0081407 A1 | 3/2022 | Stengel et al. |

OTHER PUBLICATIONS

Wehn, Paul M. et al., Design and Activity of Specific Hypoxia-Inducible Factor-2α(HIF-2α) Inhibitors for the Treatment of Clear Cell Renal Cell Carcinoma: Discovery of Clinical Candidate (S)-3-((2,2-Difluoro-1-hydroxy-7-(methylsulfony!)-2,3-dihydro-1H-inden-, Journal of Medicinal Chemistry, 2018, 9691-9721, 61.

Xu, Rui et al., 3-[(1S,2S,3R)-2,3-Difluoro-1-hydroxy-7-methylsulfonylindan-4-yl]oxy-5-fluorobenzonitrile (PT2977), a Hypoxia-Inducible Factor 2α (HIF-2α) Inhibitor for the Treatment of Clear Cell Renal Cell Carcinoma, Journal of Medicinal Chemistry, 2019, 6876-6893, 62.

*Primary Examiner* — Taofiq A Solola
(74) *Attorney, Agent, or Firm* — Eric A. Meade; John C. Todaro

(57) ABSTRACT

The disclosure provides crystalline forms for certain synthetic intermediates for making belzutifan, a HIF-2α inhibitor, useful for the treatment of cancer. The disclosure also provides processes for isolating the crystalline forms.

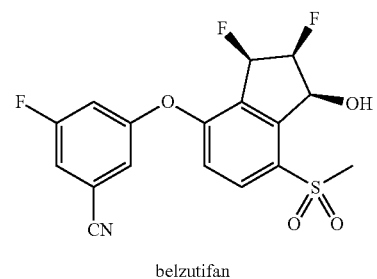

belzutifan

28 Claims, 8 Drawing Sheets

SYNTHETIC PATHWAY TO BELZUTIFAN AND CRYSTALLINE PHASES OF SYNTHETIC INTERMEDIATES

CROSS-REFERENCE TO RELATED APPLICATIONS

This patent application, is a Nonprovisional application under 35 USC 111(a) which claims the benefit of priority of U.S. Provisional Application No. 63/191,356, filed May 21, 2021.

FIELD OF THE INVENTION

The present disclosure relates to crystalline forms of certain synthetic intermediates which are valuable in the preparation of the oncology agent belzutifan. The present application also relates to certain processes that result in the isolation of such crystalline forms.

BACKGROUND OF THE INVENTION

Intratumoral hypoxia is a driving force in cancer progression and is closely linked to poor patient prognosis and resistance to chemotherapy and radiation treatment. Hypoxia-Inducible Factors (HIF-1α and HIF-2α) are transcription factors that play central roles in the hypoxic response pathway. Under normoxic conditions, the tumor suppressor von Hippel-Lindau (VHL) protein binds to specific hydroxylated proline residues and recruits the E3 ubiquition-ligase complex that targets HIF-α proteins for proteasomal degradation. Under hypoxic conditions, HIF-α proteins accumulate and enter the nucleus to stimulate the expression of genes that regulate anaerobic metabolism, angiogenesis, cell proliferation, cell survival, extracellular matrix remodeling, pH homeostasis, amino acid and nucleotide metabolism, and genomic instability. VHL deficiency can also result in accumulated HIF expression under oxygenated conditions (pseudohypoxic conditions). Accordingly, directly targeting HIF-α proteins offers an exciting opportunity to attack tumors on multiple fronts (Keith, et al., *Nature Rev. Cancer* 12: 9-22, 2012).

Specifically, HIF-2a is a key oncogenic driver in clear cell renal cell carcinoma (ccRCC) (Kondo, K., et al., *Cancer Cell*, 1:237-246 (2002); Maranchie, J. et al, *Cancer Cell*, 1:247-255 (2002); Kondo, K., et al., *PLoS Biol.*, 1:439-444 (2003)). In mouse ccRCC tumor models, knockdown of HIF-2α expression in pVHL (von Hippel-Lindau protein) defective cell lines blocked tumor growth comparable to reintroduction of pVHL. In addition, expression of a stabilized variant of HIF-2α was able to overcome the tumor suppressive role of pVHL.

Von-Hippel Lindau disease (VHL disease) is another disorder in which HIF-2α plays a significant role. VHL disease is an autosomal dominant syndrome that not only predisposes patients to kidney cancer (~70% lifetime risk), but also to hemangioblastomas, pheochromocytoma and pancreatic neuroendocrine tumors. VHL disease results in tumors with constitutively active HIF-α proteins with the majority of these dependent on HIF-2α activity (Maher, et al. *Eur. J. Hum. Genet.* 19: 617-623, 2011). HIF-2α has been linked to cancers of the retina, adrenal gland and pancreas through both VHL disease and activating mutations.

3-[(1S,2S,3R)-2,3-Difluoro-1-hydroxy-7-methylsulfonyl-indan-4-yl]oxy-5-fluoro-benzonitrile (hereinafter, belzutifan), a novel HIF-2α inhibitor with excellent in vitro potency, pharmacokinetic profile and in vivo efficacy in mouse models, has shown encouraging outcomes in patients with advanced renal cell carcinoma (Xu, Rui, et al., *J. Med. Chem.* 62:6876-6893 (2019). U.S. application Ser. No. 17/017,864, filed Sep. 11, 2020 discloses methods for preparing certain 2,3-difluoro indane derivatives, including belzutifan.

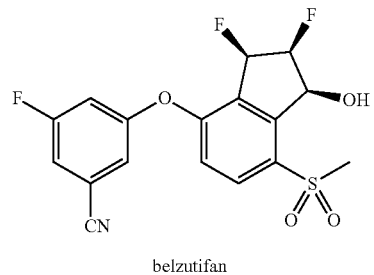 [SMILES: CS(=O)(=O)c1ccc(Oc2cc(F)cc(C#N)c2)c2c1[C@H](O)[C@H](F)[C@@H]2F]

belzutifan

The physical attributes of chemical intermediates, such as solubility, stability, melting point, and the like can be affected by the solid-state form. The present invention provides novel crystalline forms of certain synthetic intermediates of belzutifan described herein, which, surprisingly and advantageously exhibit improved thermodynamic stability while maintaining good chemical stability and other advantageous properties, as described herein.

SUMMARY OF THE DISCLOSURE

The present disclosure provides certain synthetic intermediates of belzutifan which have advantageous features, such as stability, ease of processing, and ease of handling. In certain embodiments the disclosure provides specific crystalline forms of the following synthetic intermediates:

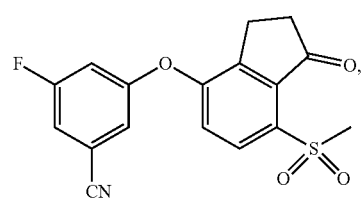

6

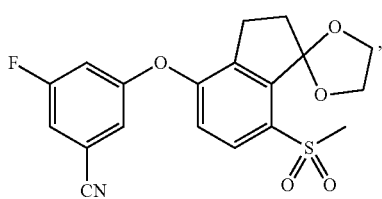

7

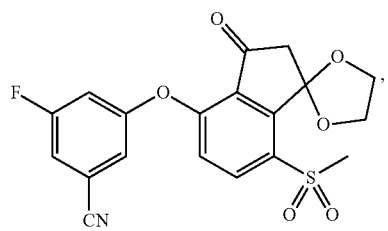

10

-continued

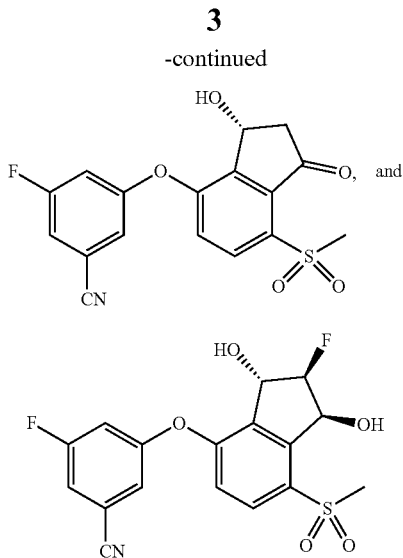

(which are also referred to herein as the crystalline forms of the present disclosure).

The disclosure furthermore provides processes for isolating the desired crystalline synthetic intermediates and processes for their conversion to the drug substance belzutifan.

DETAILED DESCRIPTION OF THE INVENTION

Figure 1:
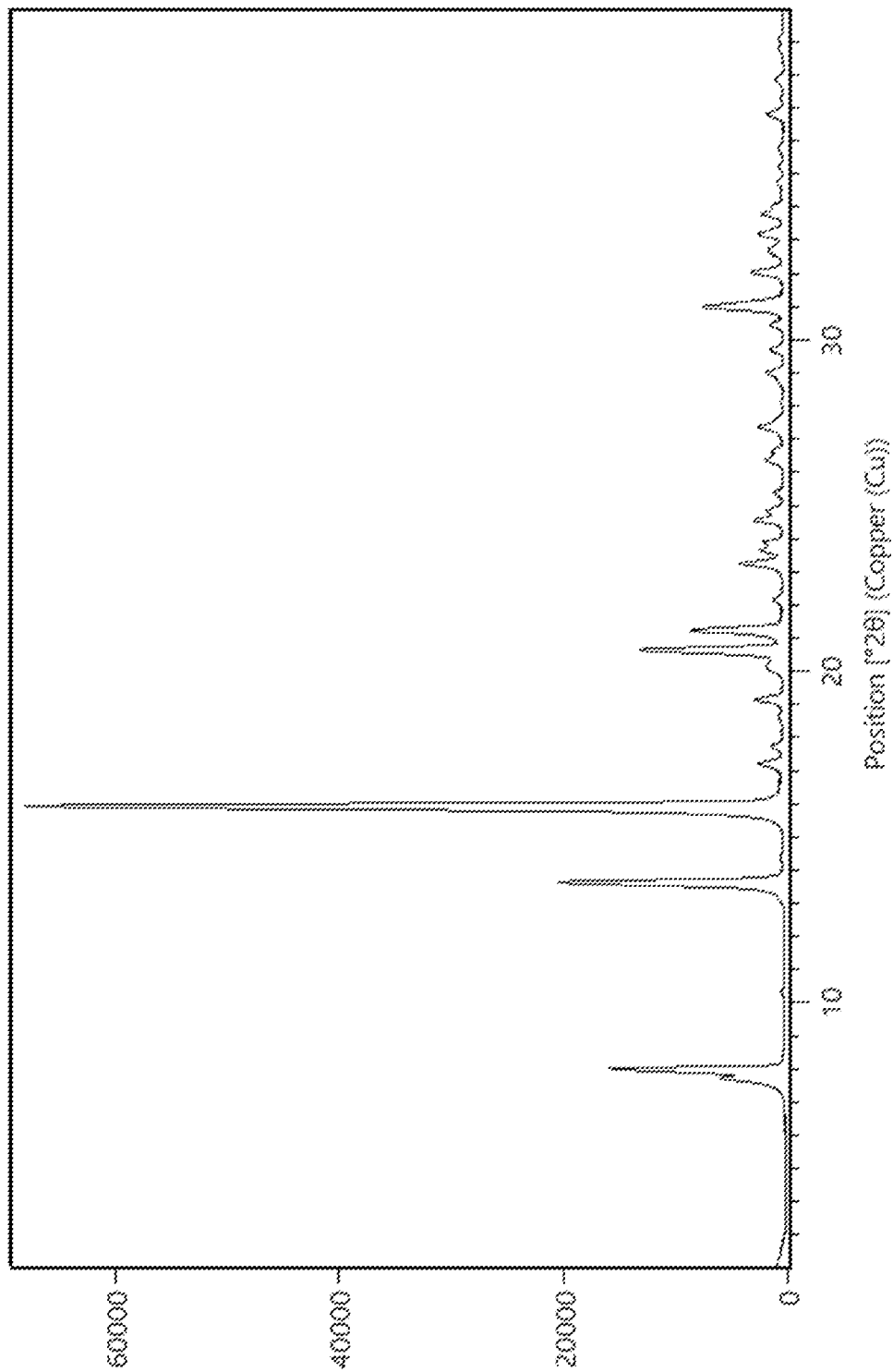
FIG. 1 is the X-ray powder diffraction (XRPD) pattern of form I of compound 6.

Crystalline Forms of the Present Disclosure and Processes for Preparing and Isolating the Crystalline Forms In a first aspect, the present disclosure provides a crystalline polymorphic form of the compound of formula 6

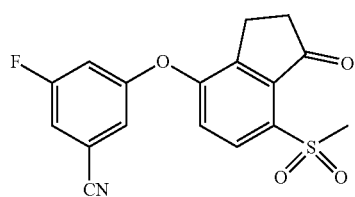

which is designated Form I, wherein the crystalline polymorphic form designated Form I has d-spacings determined by x-ray powder diffraction, Cu Kα, of about 11.0, 6.5 and 5.6 angstroms.

In one embodiment of this first aspect, the crystalline polymorphic form has at least two additional d-spacings determined by x-ray powder diffraction, Cu Kα, selected from about 11.4, 4.2, 3.8, and 2.9 angstroms.

In an embodiment of this first aspect, the crystalline polymorphic form has a Differential Scanning Calorimetry (DSC) extrapolated onset melting temperature of about 185.8° C. In one embodiment of this first aspect, the crystalline polymorphic form has a DSC peak melting temperature of about 187.6° C.

In another embodiment of this first aspect, the present disclosure provides a process for preparing the crystalline polymorphic form, comprising:

providing a slurry of the compound of formula 6 in isopropyl alcohol; and isolating the crystalline polymorphic form.

In a second aspect, the present disclosure provides a crystalline polymorphic form of the compound of formula 7

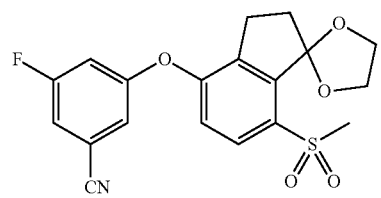

which is designated Form I, wherein the crystalline polymorphic form designated Form I has d-spacings determined by powder diffraction, Cu Kα, of about 13.1, 5.7, and 3.9 angstroms.

In one embodiment of this second aspect, the crystalline polymorphic form has at least two additional d-spacings determined by x-ray powder diffraction, Cu Kα, selected from about 6.7, 5.2, 5.1, 4.2, 4.0, or 3.8 angstroms.

In an embodiment of this second aspect, the crystalline polymorphic form has a DSC extrapolated onset melting temperature of about 167.6° C. In one embodiment of this second aspect, the crystalline polymorphic form has a DSC peak melting temperature of about 169.9° C.

In another embodiment of this second aspect, the present disclosure provides a process for preparing the crystalline polymorphic form, comprising:

providing a solution of the compound of formula 7 in isopropyl alcohol;

allowing the crystalline polymorphic form to precipitate; and isolating the precipitated crystalline polymorphic form.

In a third aspect, the present disclosure provides a crystalline polymorphic form of the compound of formula 10

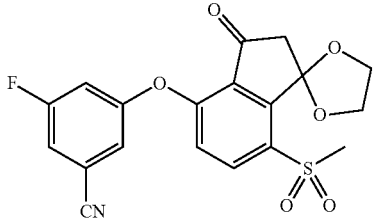

which is designated Form I, wherein the crystalline polymorphic form designated Form I has d-spacings determined by powder diffraction, Cu Kα, of about 13.1, 5.4, and 3.9 angstroms.

In one embodiment of the third aspect, the crystalline polymorphic form has at least two additional d-spacings determined by x-ray powder diffraction, Cu Kα, selected from about 9.1, 6.3, 5.1, 4.1, and 3.7 angstroms.

In an embodiment of the third aspect, the crystalline polymorphic form has a DSC extrapolated onset melting temperature of about 236.7° C. In one embodiment of the third aspect, the crystalline polymorphic form has a DSC peak melting temperature of about 238.2° C.

In another embodiment of this third aspect, the present disclosure provides a process for preparing the crystalline polymorphic form, comprising:

providing a solution of the compound of formula 10 in isopropyl alcohol and water;

allowing the crystalline polymorphic form to precipitate; and isolating the precipitated crystalline polymorphic form.

In a fourth aspect, the present disclosure provides a crystalline polymorphic form of the compound of formula 11

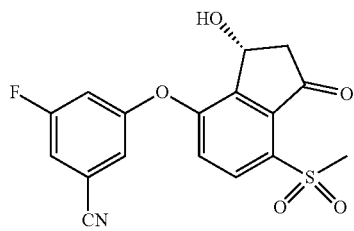

11 which is designated Form I, wherein the crystalline polymorphic form designated Form I has d-spacings determined by powder diffraction, Cu Kα, of about 12.8, 6.0, and 4.2 angstroms.

In one embodiment of the fourth aspect, the crystalline polymorphic form has at least two additional d-spacings determined by x-ray powder diffraction, Cu Kα, selected from about 9.6, 7.8, 4.4, 3.8, and 3.7 angstroms.

In an embodiment of the fourth aspect, the crystalline polymorphic form has a DSC extrapolated onset melting temperature of about 180.9° C. In one embodiment of the fourth aspect, the crystalline polymorphic form has a DSC peak melting temperature of about 182.9° C.

In another embodiment of this fourth aspect, the present disclosure provides a process for preparing the crystalline polymorphic form, comprising:

providing a slurry of the compound of formula 11 in acetonitrile and water; and isolating the crystalline polymorphic form.

In a fifth aspect, the present disclosure provides a crystalline polymorphic form of the compound of of formula 12

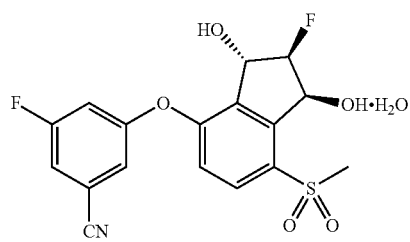

12 which is designated Hydrate Form I, wherein the crystalline polymorphic form designated Hydrate Form I has d-spacings determined by powder diffraction, Cu Kα, of about 5.5, 5.3, 4.0, and 3.9 angstroms.

In one embodiment of the fifth aspect, the crystalline polymorphic form has at least two additional d-spacings determined by x-ray powder diffraction, Cu Kα, selected from about 4.7, 3.7, 3.6, 3.4 and 3.1 angstroms.

In another embodiment of the fifth aspect, the present disclosure provides a process for preparing the crystalline polymorphic form comprising:

providing a slurry of the compound of formula 12 in acetonitrile and water;

allowing the crystalline polymorphic form to precipitate; and isolating the precipitated crystalline polymorphic form.

In a sixth aspect, the present disclosure provides a crystalline polymorph of formula 12

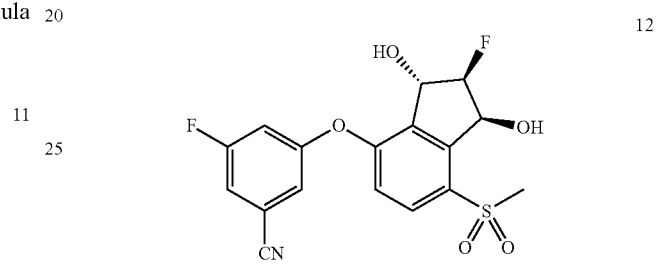

12 which is designated Form I, wherein the crystalline polymorphic form designated Form I has d-spacings determined by powder diffraction, Cu Kα, of about 11.4, 6.0, 5.8, and 4.4 angstroms. In one embodiment of the sixth aspect, the crystalline polymorphic form has at least two additional d-spacings determined by x-ray powder diffraction, Cu Kα, selected from about 4.1, 3.9, 3.8, 3.7, and 3.6 angstroms.

In an embodiment of the sixth aspect, the crystalline polymorphic form has a DSC extrapolated onset melting temperature of about 173.3° C. In one embodiment of the sixth aspect, the crystalline polymorphic form has a DSC peak melting temperature of about 177.2° C.

In another embodiment of the sixth aspect, the present disclosure provides a process for preparing the crystalline polymorphic form comprising:

providing a solution of the compound of formula 12 in n-heptane and ethyl acetate;

allowing the crystalline polymorphic form to precipitate; and isolating the precipitated crystalline polymorphic form.

Methods of Preparing of Preparing Belzutifan and Intermediates of Belzutifan

Several methods for preparing and isolating the crystalline forms of the present disclosure are described in the following Schemes and Examples. Starting materials and intermediates are purchased, made from known procedures, or as otherwise illustrated.

Scheme 1

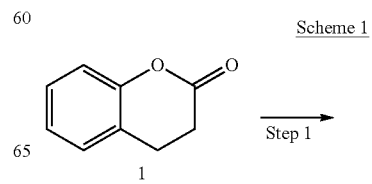

Step 1

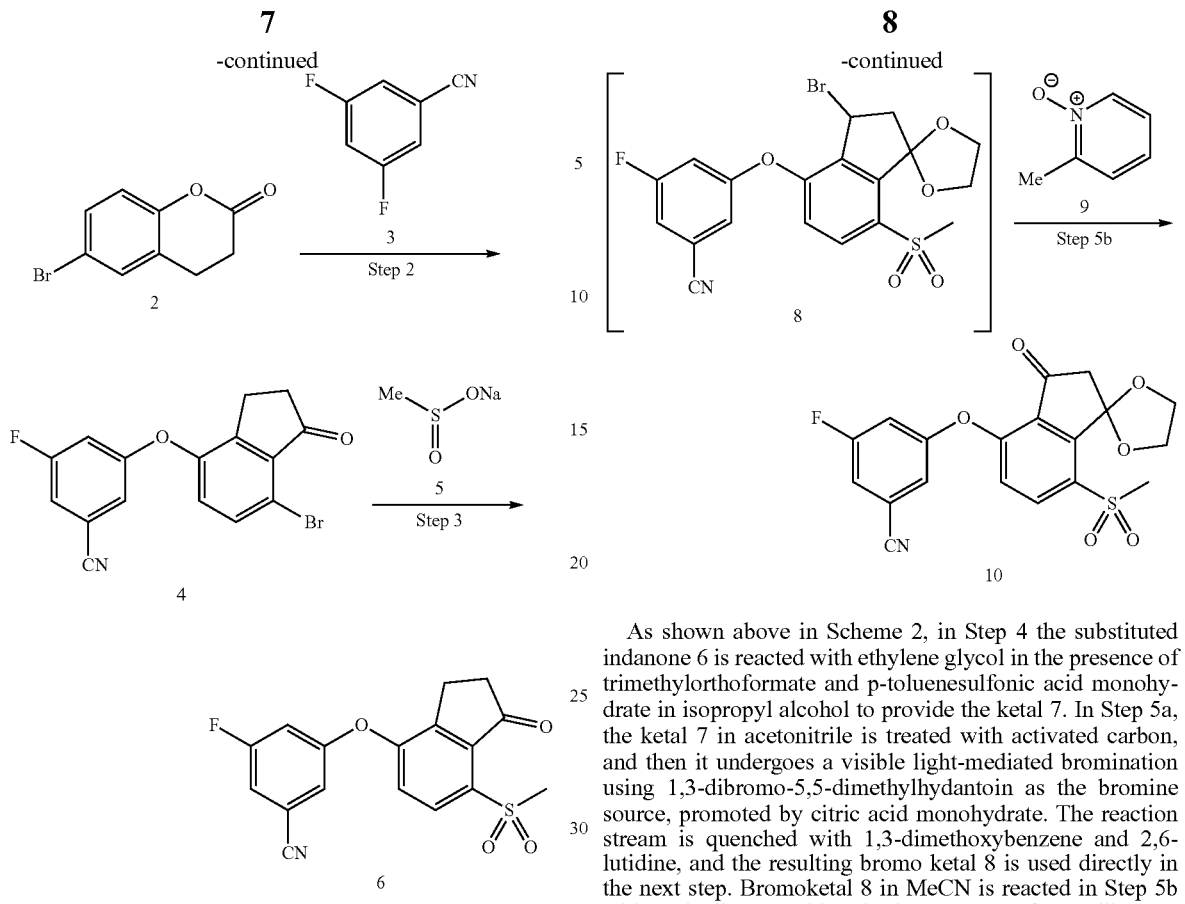

As shown above in Scheme 1, the dihydrocoumarin starting material 1 is brominated in Step 1 using, for example, N-bromosuccinimide to provide the 6-bromo-2-chromanone intermediate 2. Intermediate 2 is first reacted with water and potassium carbonate, then reacted with difluorobenzonitrile reagent 3, and then reacted with aluminum trichloride to provide the substituted indanone intermediate 4. Intermediate 4 is then treated with sodium methanesulfinate 5 in Step 3 to yield the substituted indanone 6.

As shown above in Scheme 2, in Step 4 the substituted indanone 6 is reacted with ethylene glycol in the presence of trimethylorthoformate and p-toluenesulfonic acid monohydrate in isopropyl alcohol to provide the ketal 7. In Step 5a, the ketal 7 in acetonitrile is treated with activated carbon, and then it undergoes a visible light-mediated bromination using 1,3-dibromo-5,5-dimethylhydantoin as the bromine source, promoted by citric acid monohydrate. The reaction stream is quenched with 1,3-dimethoxybenzene and 2,6-lutidine, and the resulting bromo ketal 8 is used directly in the next step. Bromoketal 8 in MeCN is reacted in Step 5b with 2-picoline N-oxide 9 in the presence of N,N-diisopropylethylamine to provide the keto ketal 10.

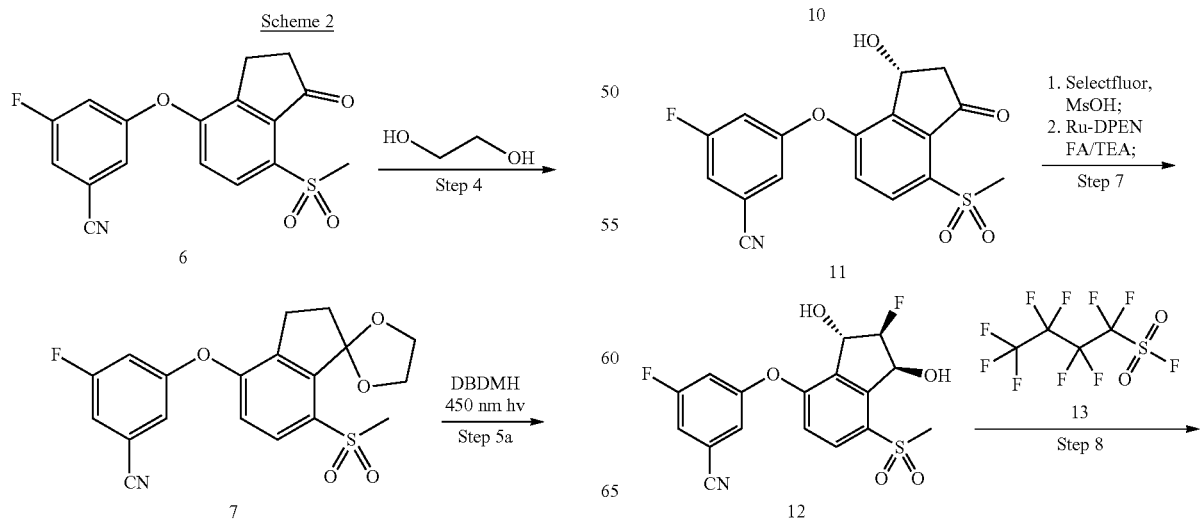

-continued

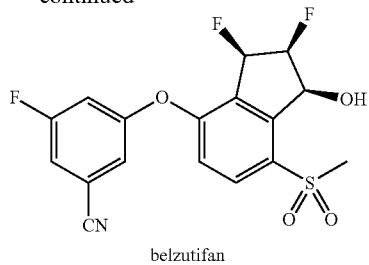
belzutifan

As shown in Scheme 3 above, the keto ketal intermediate 10 is converted to belzutifan in three steps. In Step 6, the keto ketal 10 in MeCN undergoes an asymmetric transfer hydrogenation using RuCl(p-cymene)[(R,R)-Ts-DPEN] catalyst (Ru-DPEN), triethylamine (TEA), and formic acid (FA) in the presence of water. Reaction with aqueous hydrochloric acid (HCl) then provides hydroxy indanone 11. In Step 7, the hydroxy indanone 11 is reacted with 1-chloromethyl-4-fluoro-1,4-diazoniabicyclo[2.2.2]octane bis(tetrafluoroborate) (Selectfluor) in the presence of methanesulfonic acid (MsOH) in a mixture of methanol (MeOH) and MeCN, followed by addition of water. Further reaction with Ru-DPEN, TEA, and FA affords the fluoro diol 12. In Step 8, perfluorobutanesulfonyl fluoride is combined with the fluorodiol in 1,2-dimethoxyethane (DME), and then 1,8-diazabicyclo[5.4.0]undec-7-ene (DBU) is added to yield belzutifan.

Throughout the synthetic schemes and examples, abbreviations and acronyms may be used with the following meanings unless otherwise indicated:
DBDMH=1,3-dibromo-5,5-dimethylhydantoin; DBU=1,8-diazabicyclo[5.4.0]undec-7-ene; DIEA/DIPEA=N,N-diisopropylethylamine; DME=1,2-dimethoxyethane; EDTA=ethylenediaminetetraacetic acid; FA=formic acid; IPA=isopropanol; MeCN=acetonitrile; MeOH=methanol; MsOH=methanesulfonic acid; NMP=N-methyl-2-pyrrolidone; RT=room temperature; Ru-DPEN=RuCl(p-cymene)[(R,R)-Ts-DPEN] catalyst; Selectfluor=–chloromethyl-4-fluoro-1,4-diazoniabicyclo[2.2.2]octane bis(tetrafluoroborate); TEA=triethylamine; TsOH=p-toluenesulfonic acid.

EXAMPLES

The compounds and crystalline forms thereof described herein can be prepared according to the procedures of the following schemes and examples, using appropriate materials and are further exemplified by the following specific examples. The examples further illustrate details for the preparation of the compounds and crystalline forms of the present disclosure. Those skilled in the art will readily understand that known variations of the conditions and processes of the following preparative procedures can be used to prepare these compounds and their crystalline forms. These examples are provided for the purpose of further illustration only and are not intended to be limitations on the disclosure.

Concentration refers to the removal of the volatile components at reduced pressure (e.g., by rotary evaporation) unless otherwise noted. All temperatures are in degrees Celsius unless otherwise noted. Mass spectra (MS) were measured by electrospray ion-mass spectroscopy (ESI) in positive ion detection mode and m/z refers to the [M+H]$^+$ ion unless otherwise noted. $^1$H NMR spectra were recorded at 400-500 MHz at ambient temperature unless otherwise noted. Protons reported as 0.5H are due to rotameric signals.

Powder X-ray Diffraction data were acquired on either i) a Panalytical X-pert Pro PW3040 system in the Bragg-Brentano configuration equipped with a Cu radiation source (with monochromatization to Kα achieved using a Nickel filter) and fixed slit optical configuration or ii) a Panalytical Empyrean system in the Bragg-Brentano configuration equipped with a Cu radiation source (with monochromatization to Kα achieved using Bragg-Brentano$^{HD}$ optics) and a programmable divergence slit. Data were acquired between 2 and 40° 2θ. Samples were prepared by gently pressing powdered sample onto a zero background silicon holder. Tables 1-8 below lists the XRPD peak locations for the isolated crystalline forms. The tables provide the peak positions (expressed in degrees 2θ) and D-Spacings (expressed in angstroms).

Differential scanning calorimetry (DSC) for compounds 6, 7, 10, 11 and 12 (Hydrate Form I and Methanolic Solvate I) were determined using a TA Instruments Q200 or Discovery calorimeter at a heating rate of 10° C./min under a nitrogen atmosphere in an aluminum pan with pin holes.

Differential scanning calorimetry (DSC) for compound 12, Form I, was determined using a Mettler Toledo DSC822e calorimeter at a heating rate of 5° C./min under a nitrogen atmosphere in an aluminum pan with pin holes.

The extrapolated onset and peak melting temperatures and enthalpy of each thermal event were determined for each form.

Example 1: Preparation of Form I of 3-Fluoro-5-((7-(methylsulfonyl)-1-oxo-2,3-dihydro-1H-inden-4-yl)oxy)benzonitrile (Compound 6, Form I)

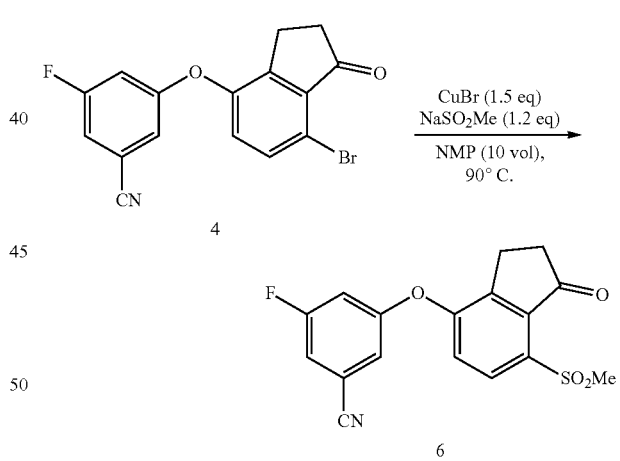

A flask was charged with NMP (830 mL, 10 vol), 4 (83.0 g, 235 mmol, 1.0 eq), CuBr (51.6 g, 352 mol, 1.5 eq), and NaSO$_2$Me (30.6, 282 mmol, 1.2 eq). The reaction mixture was heated to 90° C. for 15 h before being cooled to RT. EDTA-Na$_2$ (8 wt % aq, 664 mL) was added, and the mixture was extracted with EtOAc (1040 mL). EtOAc (400 mL) was added and the mixture was washed with 8 wt % EDTA-Na$_2$ (8 wt % aq, 300 mL). The organics were then treated with C-941 activated carbon, filtered and then concentrated to 3 vol in vacuo at 40° C. IPA (450 mL) was charged over 4 h, and the resulting slurry was agitated for an additional 3 h before being filtered. The cake was washed with IPA (2×95 mL) and dried at 50° C. under reduced pressure to afford 6 as a white solid (65.4 g, 75% yield). $^1$H NMR (400 MHz, CDCl$_3$) δ 7.99 (d, J=8 Hz, 1H), 7.79 (m, 1H), 7.61 (dd, J=4, 12 Hz, 2H), 7.45 (d, J=8 Hz, 1H), 3.42 (s, 3H), 3.08 (t, J=8, 4 Hz, 2H), 2.82 (m, 2H). $^{13}$C NMR (100 MHz, CDCl$_3$) δ 203.6, 164.3, 161.9, 157.6, 157.3, 157.2, 149.3, 136.6, 133.5, 130.7, 122.6, 120.0, 117.5, 116.5, 116.3, 114.5, 114.4, 113.4, 113.2, 43.2, 36.8, 23.1. $^{19}$F NMR (377 MHz, DMSO-d$_6$) δ −107.3. HRMS: m/z calcd for C$_{17}$H$_{12}$O$_4$NFS: (M+H)$^+$ 346.0544, found: 346.0549.

FIG. 1 shows the X-ray powder diffraction (XRPD) pattern of form I of compound 6. The 2θ positions and d-spacings are provided in Table 1 below.

TABLE 1

X-Ray Powder Diffraction 2θ Positions and D-Spacing for Crystalline Phase

| Pos. [°2θ] | d-spacing [Å] |
|---|---|
| 8.0 | 11.0 |
| 13.6 | 6.5 |
| 15.9 | 5.6 |
| 7.7 | 11.4 |
| 21.2 | 4.2 |
| 23.3 | 3.8 |
| 31.0 | 2.9 |
| 17.2 | 5.2 |
| 17.7 | 5.0 |
| 19.2 | 4.6 |
| 20.1 | 4.4 |
| 20.6 | 4.3 |
| 22.2 | 4.0 |
| 23.7 | 3.8 |
| 23.9 | 3.7 |
| 24.5 | 3.6 |
| 25.3714 | 3.5 |
| 26.3729 | 3.4 |
| 27.3616 | 3.3 |
| 29.0039 | 3.1 |
| 29.6996 | 3.0 |
| 30.4529 | 2.9 |

Differential Scanning Calorimetry

The extrapolated endothermic onset melting and peak melting temperatures observed for Form I of Compound 6 were 185.8 and 187.6, respectively, along with ΔH=100.6 J/g.

Example 2A: Preparation of Form I of 3-Fluoro-5-((7-(methylsulfonyl)-2,3-dihydrospiro[indene-1,2'-[1,3]dioxolan]-4-yl)oxy)benzonitrile (Compound 7, Form I)

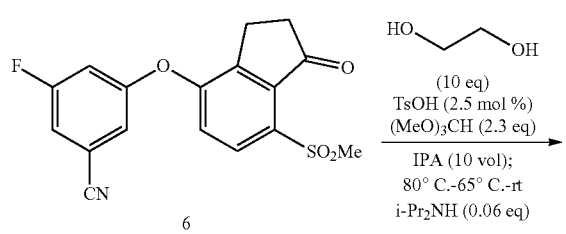

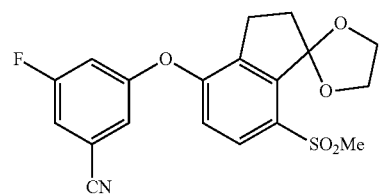

Figure 2:
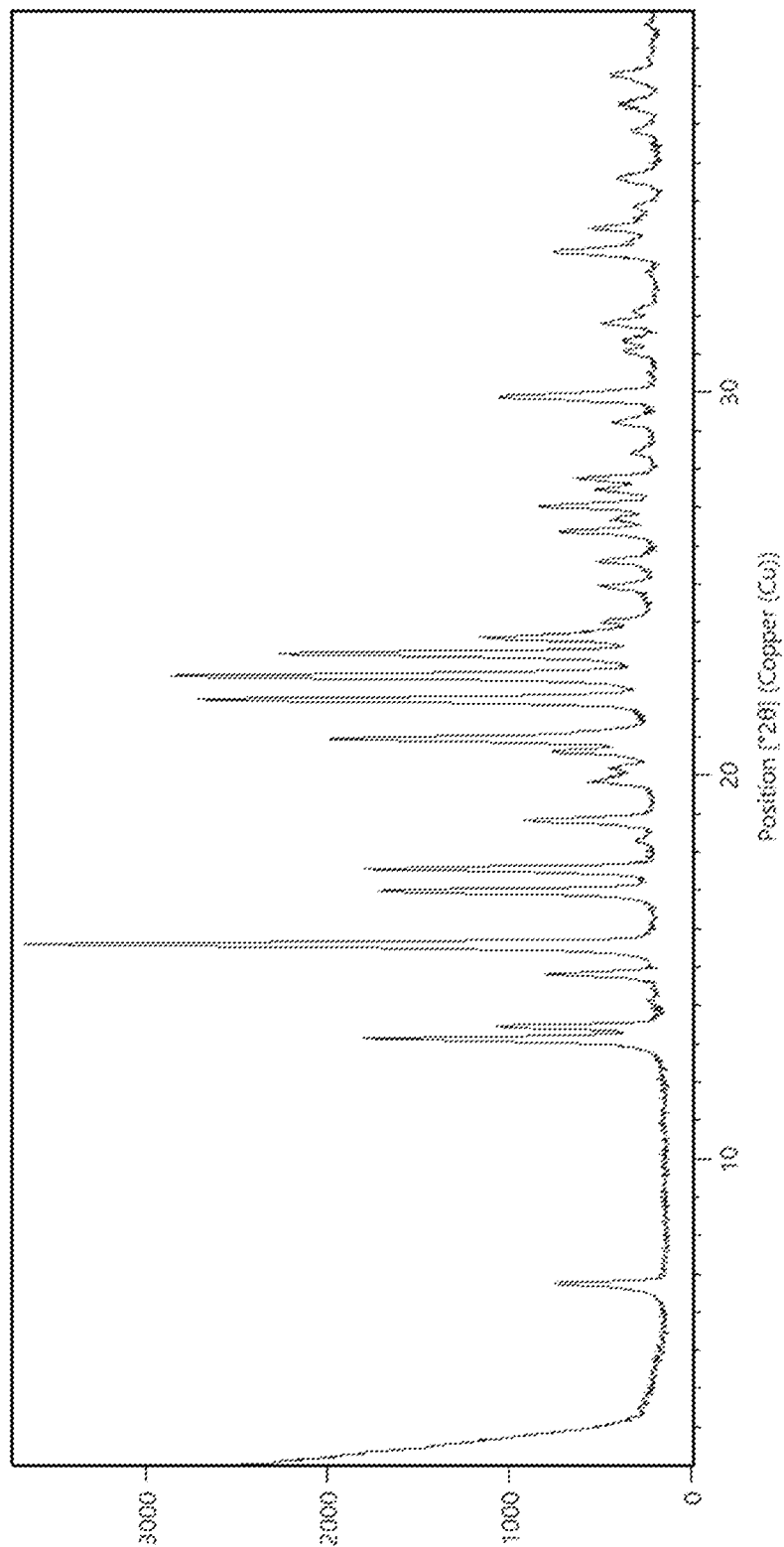
FIG. 2 is the X-ray powder diffraction (XRPD) pattern of form I of compound 7.

To a stirred suspension of indanone 6 (30.0 g, 82 mmol) in IPA (300 mL) at RT were added ethylene glycol (46.0 mL, 824 mmol) followed by trimethylorthoformate (20.7 mL, 190 mmol) and TsOH (392 mg, 2.1 mmol). The reaction was heated to 80° C. for 18 h. The reaction was then cooled to 65° C. and seeded with 0.5 wt % 7 and aged for 10 h. The resulting slurry was cooled to 25° C. over 8 h and aged an additional 3 h at 25° C. Diisopropylamine (0.693 mL, 4.95 mmol) was added and the reaction was aged for 30 min at 25° C. The reaction mixture was filtered, and the isolated product was washed three times with IPA (40.0 mL, 4 vol). The cake was dried under vacuum to give ketal 7 (27.8 g, 90.7 wt %, 64.8 mmol, 79%) as an off-white crystalline solid. $^1$H NMR (500 MHz, DMSO-d$_6$) δ 7.86 (d, J=8.6 Hz, 1H), 7.75 (m, 1H), 7.58 (s, 1H), 7.53 (dt, J=9.9, 2.2 Hz, 1H), 7.15 (d, J=8.6 Hz, 1H), 4.21 (m, 2H), 4.04 (m, 2H), 3.28 (s, 3H), 2.83 (t, J=6.7 Hz, 2H), 2.23 (t, J=6.8 Hz, 2H). $^{13}$C NMR (126 MHz, DMSO-d$_6$) δ 163.59, 161.62, 156.78 (d, J=11.7 Hz), 156.00, 142.23, 136.87, 133.09, 131.57, 119.68 (d, J=3.4 Hz), 118.10, 117.20, 117.01 (d, J=3.7 Hz), 115.80 (d, J=25.5 Hz), 113.96 (d, J=12.2 Hz), 112.92 (d, J=24.7 Hz), 64.88, 44.61, 37.21, 24.84. $^{19}$F NMR (471 MHz, DMSO-d$_6$) δ −107.35. HRMS: m/z calcd for C$_{19}$H$_{16}$O$_5$NFSH:

FIG. 2 shows the X-ray powder diffraction (XRPD) pattern of form I of compound 7. The 2θ positions and d-spacings are provided in Table 2 below.

TABLE 2

X-Ray Powder Diffraction 2θ Positions and D-Spacing for Crystalline Phase

| Pos. [°2θ] | d-spacing [Å] |
|---|---|
| 6.7 | 13.1 |
| 15.6 | 5.7 |
| 22.6 | 3.9 |
| 13.1 | 6.7 |
| 17.0 | 5.2 |
| 17.6 | 5.1 |
| 21.0 | 4.2 |
| 22.0 | 4.0 |
| 23.2 | 3.8 |
| 13.4 | 6.6 |
| 14.8 | 6.0 |
| 18.8 | 4.7 |
| 19.9 | 4.5 |
| 20.6 | 4.3 |
| 23.6 | 3.8 |
| 24.0 | 3.7 |
| 24.9 | 3.6 |
| 25.6 | 3.5 |
| 26.4 | 3.4 |
| 26.7 | 3.3 |
| 27.0 | 3.3 |
| 27.8 | 3.2 |
| 29.9 | 3.0 |

Differential Scanning Calorimetry

The extrapolated endothermic onset melting and peak melting temperatures observed for Form I of compound 7 were 167.6° C. and 169.9° C., respectively, along with ΔH=94.7 J/g.

Example 2B: Preparation of Form II of 3-Fluoro-5-((7-(methylsulfonyl)-2,3-dihydrospiro[indene-1,2'-[1,3]dioxolan]-4-yl)oxy)benzonitrile (Compound 7, Form II)

Compound 7 was prepared as described above in Example 2A but a different procedure was used used to isolate the product from the reaction mixture. After the reaction was completed, the reaction mixture was cooled, extracted with aq. sodium bicarbonate, and then water. The organic layer, containing compound 7, was solvent-swapped into IPA, which resulted in crystallization of compound 7. The isolated crystalline 7 was washed with IPA and dried in vacuo.

Figure 3:
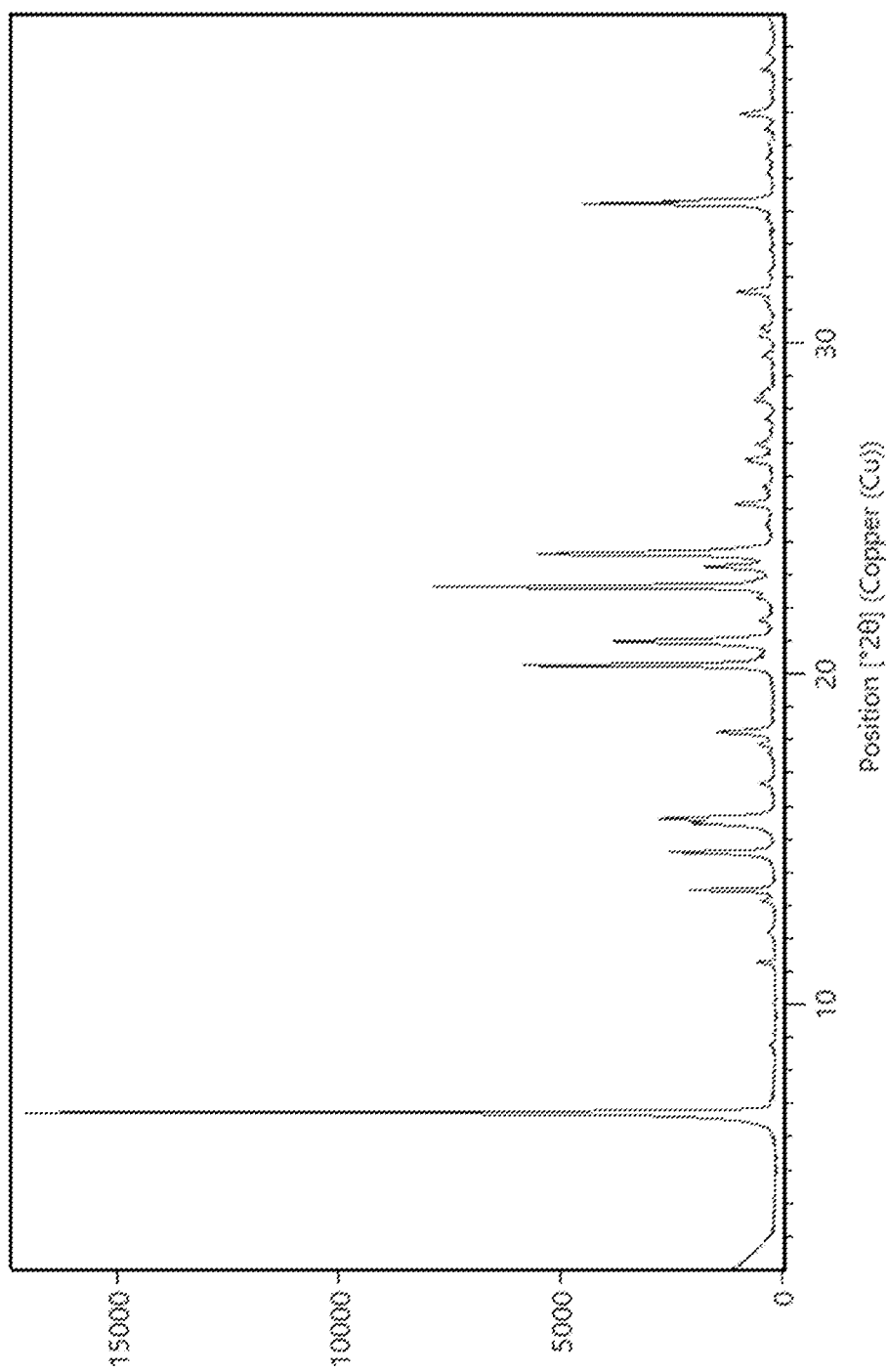
FIG. 3 is the X-ray powder diffraction (XRPD) pattern of form II of compound 7.

FIG. 3 is the X-ray powder diffraction (XRPD) pattern of form II of compound 7. The 2θ positions and d-spacings are provided in Table 3 below.

TABLE 3

X-Ray Powder Diffraction 2θ Positions and D-Spacing for Crystalline Phase

| Pos. [°2θ] | d-spacing [Å] |
| --- | --- |
| 6.7 | 13.2 |
| 20.3 | 4.4 |
| 22.6 | 3.9 |
| 13.5 | 6.6 |
| 14.6 | 6.1 |
| 15.6 | 5.7 |
| 21.0 | 4.2 |
| 23.6 | 3.8 |
| 11.3 | 7.9 |
| 13.1 | 6.7 |
| 15.5 | 5.7 |
| 16.7 | 5.3 |
| 17.9 | 5.0 |
| 18.2 | 4.9 |
| 21.6 | 4.1 |
| 22.3 | 4.0 |
| 23.2 | 3.8 |
| 25.1 | 3.5 |
| 25.6 | 3.5 |
| 26.5 | 3.4 |
| 26.9 | 3.3 |

Differential Scanning Calorimetry

The DSC of Form II shows an initial endothermic melting event (extrapolated onset=153.0° C., peak=157.7° C., ΔH=60.4 J/g) followed by an exothermic annealing/recrystallization event where Form I is produced (extrapolated onset=159.4, peak=160.2, ΔH=−8.6 J/g) and a final endothermic melting of Form I (extrapolated onset=169.1, peak=171.1, ΔH=34.8 J/g).

Example 3: Preparation of Form I of 3-Fluoro-5-((7-(methyl sulfonyl)-3-oxo-2,3-dihydrospiro[indene-1,2'-[1,3]dioxolan]-4-yl)oxy)benzonitrile (Compound 10, Form I)

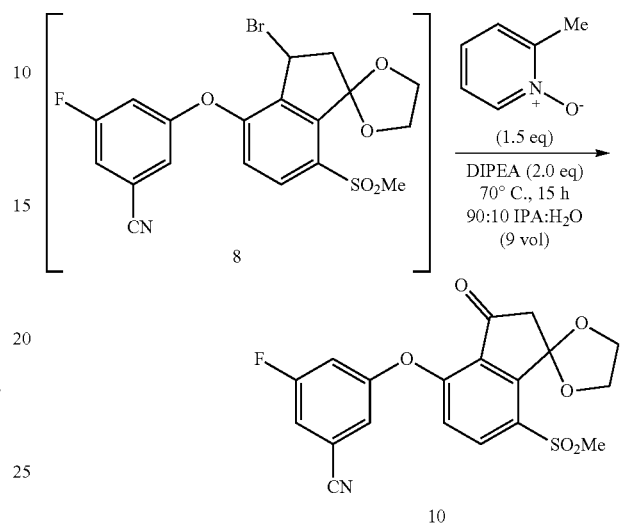

DIPEA (41.0 mL, 2.0 eq) and 2-picoline N-oxide (33.0 g, 57.9 wt % in MeCN, 1.5 eq) were charged to the crude quenched solution of 8, and the resulting dark homogeneous solution was aged at 70° C. until full consumption of 8 (typically 15-18 h). The reaction mixture was cooled to 40° C. and concentrated under vacuum to ~1.0 L. The batch was seeded with 1.0 g (2.0 wt %) of 10. After aging for 20 min at 40° C., the batch was further concentrated under vacuum to ~400 mL (8 vol) at 40° C. Constant volume distillation was carried out at 40° C. using IPA/$H_2O$ (9:1, 450 mL, 9 vol). The batch was cooled to 25° C. and aged for 15 h. The resulting slurry was filtered and the cake washed with 2:8 MeCN:IPA (4×150 mL) and dried under vacuum at 50° C. Ketone 10 (35.3 g, 97.6 wt %, 87.5 mmol, 73% yield over 2 steps) was isolated as a light brown crystalline solid. $^1$H NMR (500 MHz, $CDCl_3$) δ 8.38 (d, J=8.6 Hz, 1H), 7.24 (ddd, J=7.6, 2.3, 1.3 Hz, 1H), 7.15 (dd, J=2.1, 1.0 Hz, 1H), 7.10 (d, J=8.6 Hz, 1H), 7.07 (dt, J=9.0, 2.3 Hz, 1H), 4.51-4.41 (m, 2H), 4.18-4.08 (m, 2H), 3.27 (s, 3H), 2.94 (s, 2H). $^{13}$C NMR (126 MHz, $CDCl_3$) δ 195.58, 163.25 (d, J=253.1 Hz), 156.93 (d, J=11.1 Hz), 156.27, 151.48, 139.81, 134.66, 129.49, 120.15, 118.95 (d, J=3.7 Hz), 116.73 (d, J=3.6 Hz), 116.06 (d, J=24.8 Hz), 115.12 (d, J=11.4 Hz), 112.61 (d, J=24.4 Hz), 109.79, 66.07, 50.28, 45.14 $^{19}$F NMR (471 MHz, $CDCl_3$) δ −105.62. HRMS: m/z calcd for $C_{19}H_{14}O_6NFSH$: $(M+H)^+$ 404.0604, found: 404.0603.

Figure 4:
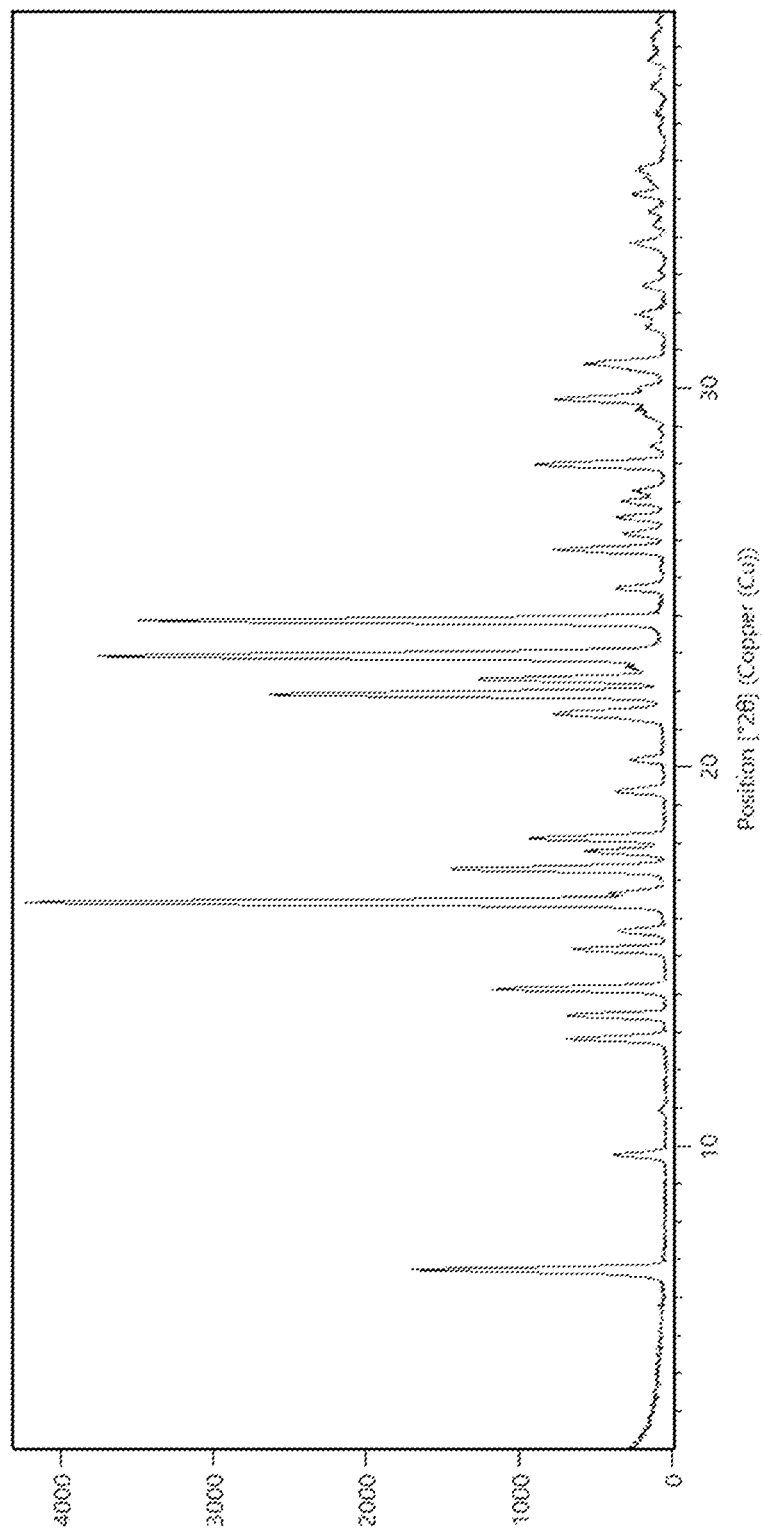
FIG. 4 is the X-ray powder diffraction (XRPD) pattern of form I of compound 10.

FIG. 4 show the X-ray powder diffraction (XRPD) pattern of form I of compound 10. The 2θ positions and d-spacings are provided in Table 4 below.

TABLE 4

X-Ray Powder Diffraction 2θ Positions and D-Spacing for Crystalline Phase

| Pos. [°2θ] | d-spacing [Å] |
| --- | --- |
| 6.7 | 13.1 |
| 16.4 | 5.4 |

TABLE 4-continued

X-Ray Powder Diffraction 2θ Positions
and D-Spacing for Crystalline Phase

| Pos. [°2θ] | d-spacing [Å] |
|---|---|
| 22.9 | 3.9 |
| 9.8 | 9.1 |
| 14.1 | 6.3 |
| 17.3 | 5.1 |
| 21.9 | 4.1 |
| 23.9 | 3.7 |
| 12.8 | 6.9 |
| 13.4 | 6.6 |
| 15.2 | 5.8 |
| 15.7 | 5.7 |
| 17.8 | 5.0 |
| 18.1 | 4.9 |
| 19.4 | 4.6 |
| 20.2 | 4.4 |
| 21.4 | 4.2 |
| 22.3 | 4.0 |
| 22.8 | 3.9 |
| 24.7 | 3.6 |
| 25.7 | 3.5 |
| 26.2 | 3.4 |
| 26.6 | 3.4 |
| 27.0 | 3.3 |
| 28.0 | 3.2 |

Differential Scanning Calorimetry

The extrapolated endothermic onset melting and peak melting temperatures observed for Form I of compound 10 were 236.7° C. and 238.2° C., respectively, along with ΔH=99.4 J/g.

Example 4: Preparation of Form I of (R)-3-Fluoro-5-((3-hydroxy-7-(methylsulfonyl)-1-oxo-2,3-dihydro-1H-inden-4-yl)oxy)benzonitrile (Form I of Compound 11)

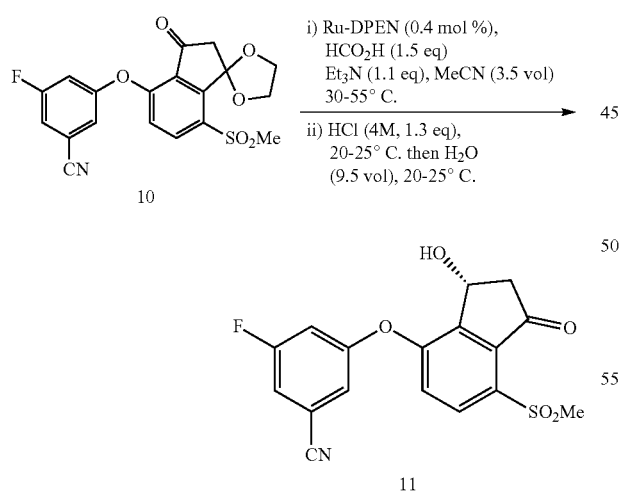

To a slurry of 10 (30.0 g, 96.6 wt %, 1.0 eq) in MeCN (105 mL, 3.5 vol) at <15° C. was added Et$_3$N (8.0 g, 1.1 eq), formic acid (4.96 g, 1.5 eq) and RuCl[(R, R)-TsDpen](p-cymene) (183 mg, 0.004 eq.). The mixture was heated at 30-35° C. with headspace N$_2$ sweep for 5 to 10 h until consumption of 10. HCl (22.4 mL, 4.18 M, 1.3 eq) was then charged at 20-25° C., and the mixture aged for 5-10 h until consumption of 10. H$_2$O (30.0 mL, 1.0 vol) was added followed by addition of 11 seed (300 mg, 1 wt %) to afford a white slurry. Additional H$_2$O (360.0 mL, 11 vol) was added over 7-9 h, and the resulting slurry was filtered and washed with H$_2$O (2×105 mL, 3 vol) and IPA (105 mL, 3 vol). The cake was dried under vacuum to afford the alcohol 11 as a white crystalline solid in 93% yield.

Hydroxy indanone product 11: $^1$H NMR (500 MHz, CD$_3$CN) δ 8.10 (d, J=10.0 Hz, 1H), 7.40 (d, J=5.0 Hz, 1H), 7.33 (m, 2H), 7.24 (d, J=10.0 Hz, 1H), 5.42 (m, 1H), 3.85 (d, J=6.0 Hz, 1H), 3.34 (s, 3H), 3.14 (dd, J=20.0 Hz, J=5.0 Hz, 1H), 2.62 (dd, J=15.0 Hz, J=10.0 Hz, 1H). $^{13}$C NMR (126 MHz, CD$_3$CN) δ 200.44, 163.1 (d, J=248.8 Hz), 157.83, 157.45 (d, J=11.5 Hz), 148.41, 136.08, 133.14, 132.46, 123.44, 119.30 (d, J=3.6 Hz), 115.50 (d, J=25.4 Hz), 114.50 (d, J=12.0 Hz), 112.40 (d, J=24.9 Hz), 64.89, 46.63, 42.54. $^{19}$F NMR (471 MHz, CD$_3$CN) δ −109.04. HRMS: m/z calcd for C$_{17}$H$_{12}$O$_5$NFSNa: (M+Na)$^+$ 384.0318, found: 384.0322.

Figure 5:
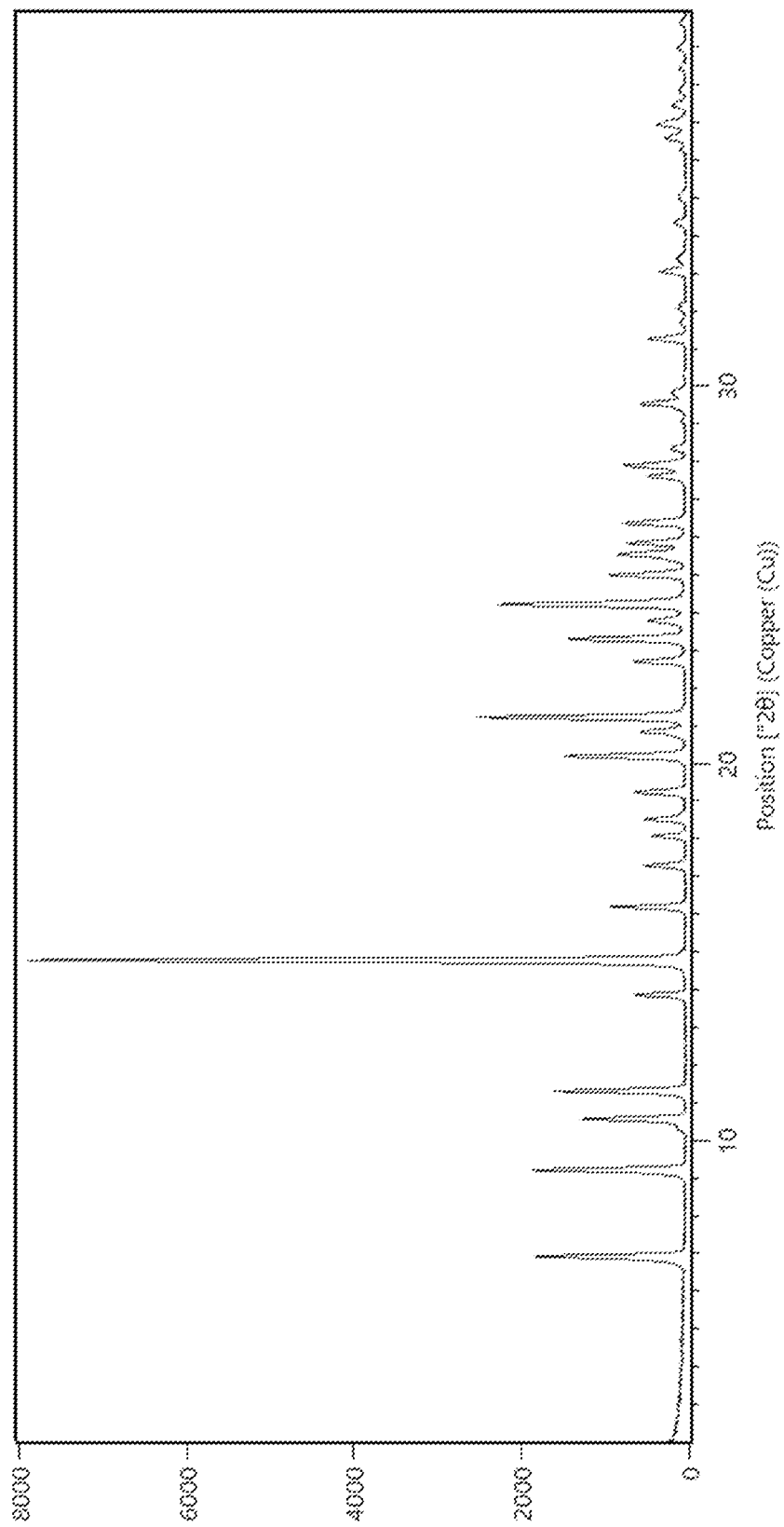
FIG. 5 is the X-ray powder diffraction (XRPD) pattern of form I of compound 11.

FIG. 5 shows the X-ray powder diffraction (XRPD) pattern of form I of compound 11. The 2θ positions and d-spacings are provided in Table 5 below.

TABLE 5

X-Ray Powder Diffraction 2θ Positions
and D-Spacing for Crystalline Phase

| Pos. [°2θ] | d-spacing [Å] |
|---|---|
| 6.9 | 12.8 |
| 14.8 | 6.0 |
| 21.2 | 4.2 |
| 9.2 | 9.6 |
| 11.3 | 7.8 |
| 20.2 | 4.4 |
| 23.3 | 3.8 |
| 24.2 | 3.7 |
| 10.6 | 8.4 |
| 13.9 | 6.4 |
| 16.2 | 5.5 |
| 17.3 | 5.1 |
| 18.1 | 5.0 |
| 18.5 | 4.8 |
| 19.2 | 4.6 |
| 20.8 | 4.3 |
| 22.7 | 3.9 |
| 23.8 | 3.7 |
| 25.0 | 3.6 |
| 25.5 | 3.5 |
| 25.8 | 3.5 |
| 26.4 | 3.4 |

Differential Scanning Calorimetry

The extrapolated endothermic onset melting and peak melting temperatures observed for Form II were 180.9 and 182.9, respectively, along with ΔH=90.7 J/g.

Example 5A: Preparation of Hydrate Form I of 3-Fluoro-5-(((1S,2R,3S)-2-fluoro-1,3-dihydroxy-7-(methylsulfonyl)-2,3-dihydro-1H-inden-4-yl)oxy)benzonitrile hydrate (Hydrate Form I of Compound 12)

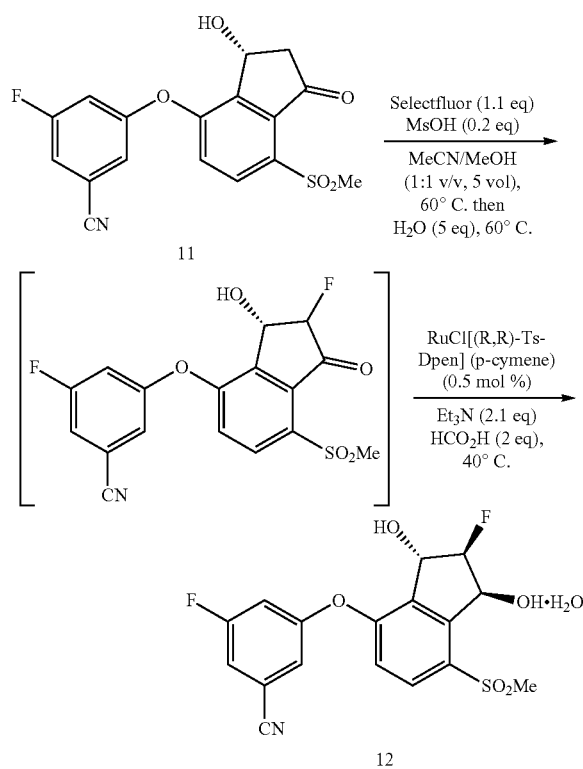

To a solution of 11 (10.0 g, 99.1 wt %, 1.0 eq.) in MeCN (25 mL) and MeOH (25 mL) were added MsOH (0.53 g, 0.356 mL, 0.2 eq) and SelectFluor (10.92 g, 97.9 wt %, 1.10 eq). The mixture was heated to 60° C. for 20 h, before $H_2O$ (2.47 mL, 5.0 eq) was added. The mixture was aged at 60° C. for a further 4 h before cooling down to 5° C. Triethylamine (8.03 mL, 2.1 eq) was added followed by formic acid (2.10 mL, 2.0 eq) and RuCl[(R, R)-TsDpen](p-cymene) (88.0 mg, 0.5 mol %). The mixture was stirred at 40° C. for 16 h, before being cooled to 30° C. and quenched with MsOH (1.78 mL, 1.0 eq). The mixture was then treated with CUNO 5 activated carbon, filtered through a pad of Solka Floc, and the cake rinsed with MeCN (50 mL). The mixture was concentrated to 50 mL under vacuum. $H_2O$ (20 mL) was added at 25° C. and the reaction was seeded with 12 hydrate (100 mg, 1%). The mixture was stirred for 3 h before slow addition of further $H_2O$ (70 mL) over 8 h. Then the slurry was cooled to 0° C. and stirred for 3 h. The resulting slurry was filtered, and the cake was washed with $H_2O$/MeCN (10:1 v/v, 2×30 mL) and dried under vacuum at 40° C. to provide fluorohydrin 12 as an off-white solid. 9.68 g, 90.97 wt %, 84.2% yield). $^1H$ NMR (500 MHz, DMSO-$d_6$) δ 7.90 (d, J=8.6 Hz, 1H), 7.70 (ddd, J=8.3, 2.4, 1.3 Hz, 1H), 7.44 (dd, J=2.6, 1.3 Hz, 1H), 7.39 (dt, J=10.0, 2.3 Hz, 1H), 7.24 (d, J=8.6 Hz, 1H), 5.93 (dd, J=7.1, 0.6 Hz, 1H), 5.84 (d, J=7.1 Hz, 1H), 5.60 (dt, J=7.1, 4.7 Hz, 1H), 5.26 (ddd, J=14.2, 7.0, 4.8 Hz, 1H), 4.91 (dt, J=51.2, 5.0 Hz, 1H) and 3.34 (s, 3H) ppm. $^{13}C$ NMR (125 MHz, DMSO-$d_6$) δ 162.5 (d, J=247.8 Hz), 157.7 (d, J=11.8 Hz), 156.4, 142.7 (d, J=2.6 Hz), 134.1 (d, J=9.2 Hz), 133.8, 131.9, 120.3, 118.8 (d, J=3.3 Hz), 117.2 (d, J=3.7 Hz), 115.0 (d, J=25.5 Hz), 113.6 (d, J=12.3 Hz), 112.0 (d, J=24.8 Hz), 98.0 (d, J=193.0 Hz), 73.5 (d, J=25.4 Hz), 69.2 (d, J=17.8 Hz), and 45.0 ppm. $^{19}F$ NMR (471 MHz, DMSO-$d_6$) δ −107.8 (t, J=9.1 Hz), and −203.0 (ddd, J=51.3, 14.3, 4.3 Hz) ppm. HRMS: m/z calcd for $C_{17}H_{12}F_2NO_4S$: $(M+H-H_2O)^+$ 364.0450, found: 364.0457.

Figure 6:
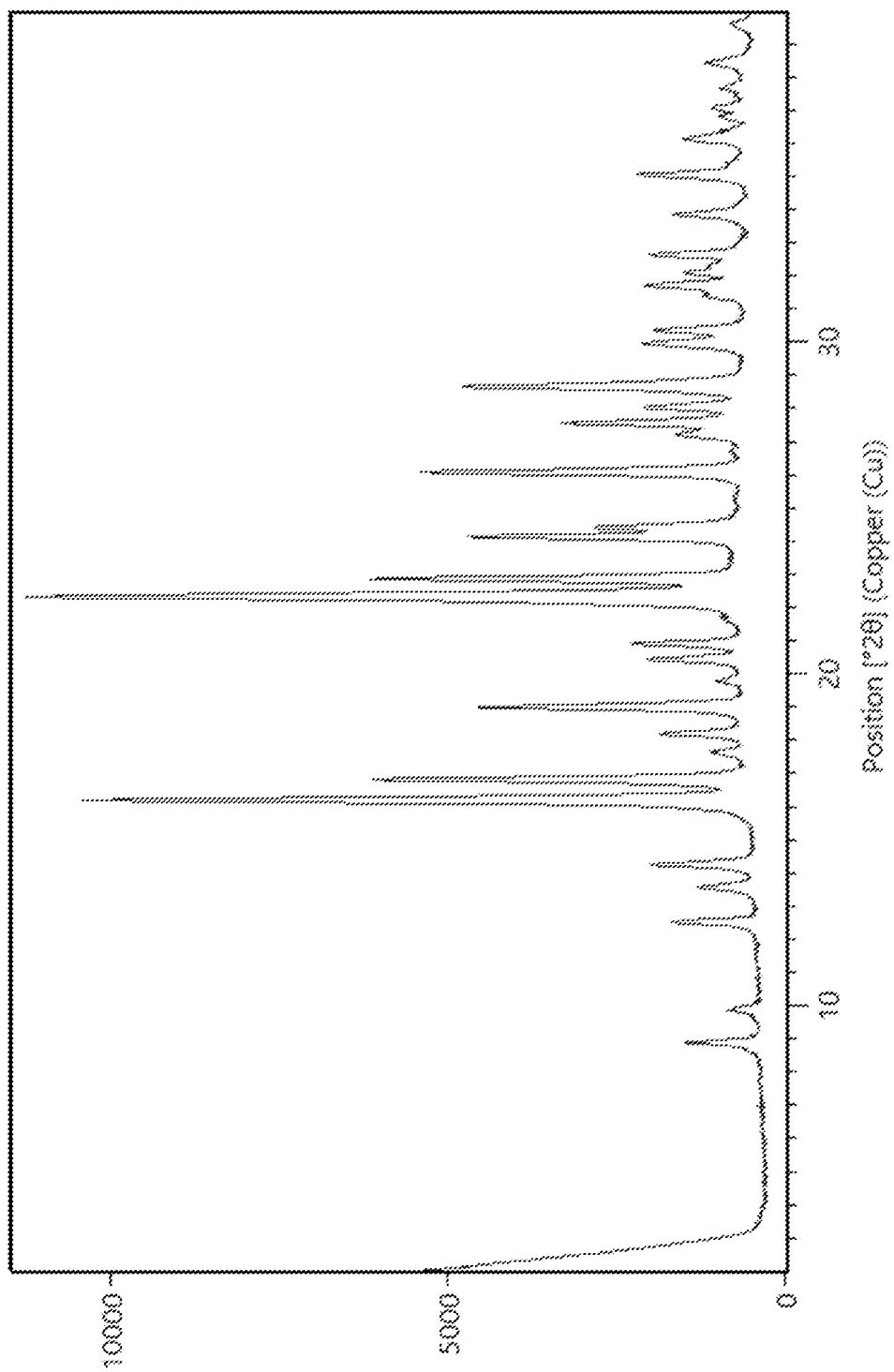
FIG. 6 is the X-ray powder diffraction (XRPD) pattern of hydrate form I of compound 12.

FIG. 6 shows the X-ray powder diffraction (XRPD) pattern of hydrate form I of compound 12. The 2θ positions and d-spacings are provided in Table 6 below.

TABLE 6

| X-Ray Powder Diffraction 2θ Positions and D-Spacing for Crystalline Phase | |
|---|---|
| Pos. [°2θ] | d-spacing [Å] |
| 16.2 | 5.5 |
| 16.8 | 5.3 |
| 22.3 | 4.0 |
| 22.9 | 3.9 |
| 19.0 | 4.7 |
| 24.1 | 3.7 |
| 24.4 | 3.7 |
| 26.1 | 3.4 |
| 28.7 | 3.1 |
| 8.9 | 10.0 |
| 9.9 | 9.0 |
| 12.5 | 7.1 |
| 13.6 | 6.5 |
| 14.2 | 6.2 |
| 17.6 | 5.0 |
| 18.2 | 4.9 |
| 20.4 | 4.4 |
| 20.9 | 4.3 |
| 27.2 | 3.3 |
| 27.6 | 3.2 |
| 28.0 | 3.2 |

Differential Scanning Calorimetry

The DSC of Hydrate Form I shows an initial broad endothermic event consistent with dehydration (extrapolated onset=26.3° C., peak=88.0° C., ΔH=437.9 J/g) followed by a second endothermic event, the melting of Form I (extrapolated onset=174.4° C., peak=177.2° C.).

Example 5B: Preparation of Methanolic Solvate Form I of 3-Fluoro-5-(((1S,2R,3S)-2-fluoro-1,3-dihydroxy-7-(methylsulfonyl)-2,3-dihydro-1H-inden-4-yl)oxy)benzonitrile hydrate (Methanolic Solvate Form I of Compound 12)

To a round bottom flask with overhead stirring was charged a reaction stream of 3-fluoro-5-(((1 S,2R,3 S)-2-fluoro-1,3-dihydroxy-7-(methylsulfonyl)-2,3-dihydro-1H-inden-4-yl)oxy)benzonitrile synthesized according to the method above on 3.3 mol scale. The mixture was quenched with MsOH and treated with CUNO 5 activated carbon (120 g). The mixture was filtered and the cake washed with MeOH (5 L). The ratio of MeCN/MeOH in the batch was 1:5 v/v. An aliquot was taken and allowed to sit at ambient temperature overnight during which a crystalline precipitate formed. The precipitate was filtered and allowed to air dry for characterization.

Figure 7:
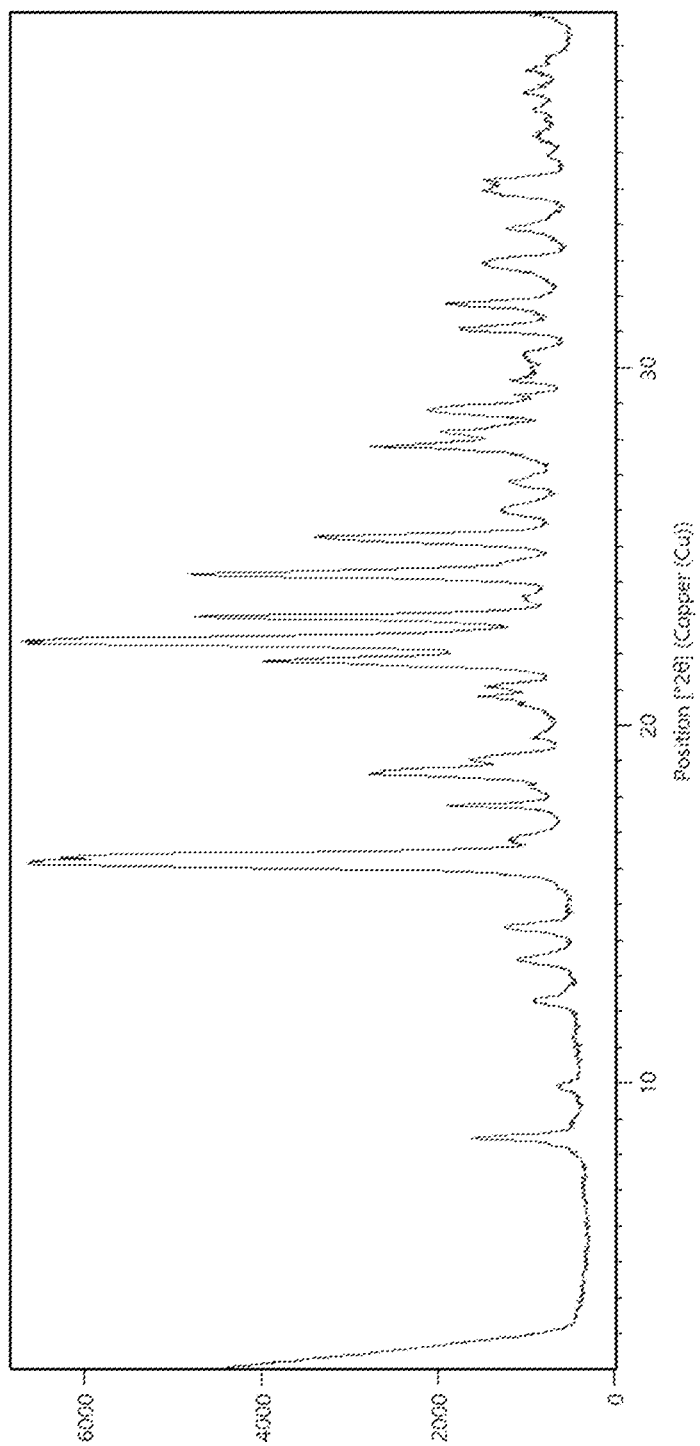
FIG. 7 is the X-ray powder diffraction (XRPD) pattern of methanolic solvate form I of compound 12.

FIG. 7 shows the X-ray powder diffraction (XRPD) pattern of methanolic solvate form I of compound 12. The 2θ positions and d-spacings are provided below in Table 7.

TABLE 7

X-Ray Powder Diffraction 2θ Positions
and D-Spacing for Crystalline Phase

| Pos. [°2θ] | d-spacing [Å] |
|---|---|
| 8.5 | 10.5 |
| 16.1 | 5.5 |
| 18.7 | 4.8 |
| 22.3 | 4.0 |
| 13.5 | 6.6 |
| 14.4 | 6.2 |
| 16.3 | 5.4 |
| 22.4 | 4.0 |
| 23.0 | 3.9 |
| 27.8 | 3.2 |
| 28.8 | 3.1 |
| 12.3 | 7.2 |
| 17.8 | 5.0 |
| 19.0 | 4.7 |
| 21.1 | 4.2 |
| 24.2 | 3.7 |
| 25.3 | 3.5 |
| 28.2 | 3.2 |
| 31.1 | 2.9 |
| 31.8 | 2.8 |

Differential Scanning Calorimetry

The DSC of Methanolic Solvate Form I shows two initial broad endothermic events, both consistent with desolvation (event 1: extrapolated onset=26.8° C., peak=71.7° C., ΔH=108.9 J/g; event 2: extrapolated onset=83.2° C., peak=90.8° C., ΔH=119.1 J/g) followed by a final endothermic event, the melting of Form I (extrapolated onset=173.9° C., peak=175.6° C.).

Example 5C: Preparation of Anhydrous Form I of 3-Fluoro-5-(((1S,2R,3S)-2-fluoro-1,3-dihydroxy-7-(methylsulfonyl)-2,3-dihydro-1H-inden-4-yl)oxy) benzonitrile hydrate (Form I of Compound 12)

Form I of 12 crystallized and was isolated from a mixture of ethyl acetate and n-heptane (as antisolvent).

Figure 8:
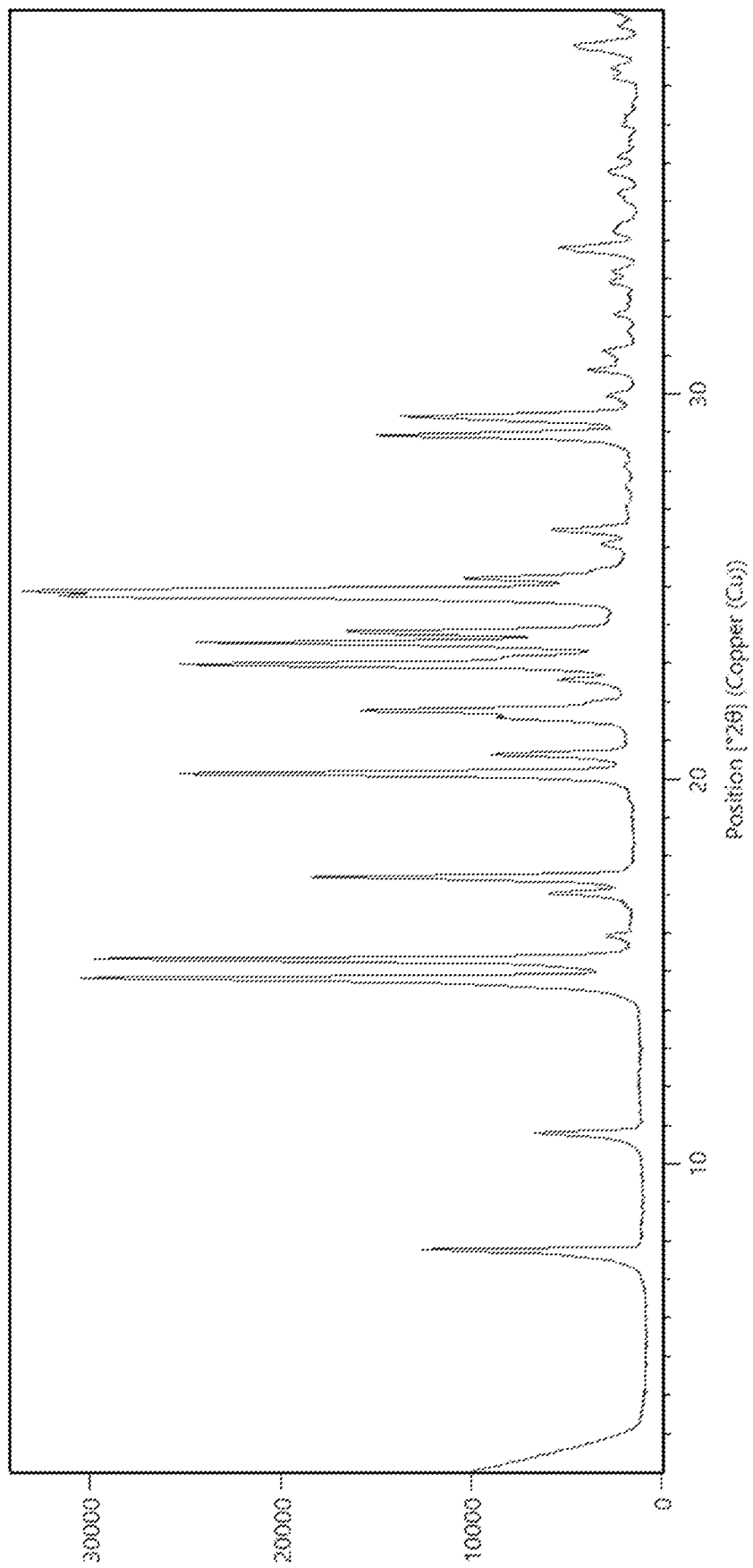
FIG. 8 is the X-ray powder diffraction (XRPD) pattern of form I of compound 12.

FIG. 8 shows the X-ray powder diffraction (XRPD) pattern of form I of compound 12. The 2θ positions and d-spacings are provided in Table 8 below.

TABLE 8

X-Ray Powder Diffraction 2θ Positions
and D-Spacing for Crystalline Phase

| Pos. [°2θ] | d-spacing [Å] |
|---|---|
| 7.8 | 11.4 |
| 14.8 | 6.0 |
| 15.3 | 5.8 |
| 20.1 | 4.4 |
| 21.8 | 4.1 |
| 23.0 | 3.9 |
| 23.5 | 3.8 |
| 23.8 | 3.7 |
| 24.8 | 3.6 |
| 24.9 | 3.6 |
| 10.8 | 8.2 |
| 17.0 | 5.2 |
| 17.5 | 5.1 |
| 20.6 | 4.3 |
| 22.6 | 3.9 |
| 25.2 | 3.5 |
| 26.5 | 3.4 |
| 28.9 | 3.1 |
| 29.4 | 3.0 |
| 33.8 | 2.7 |

Differential Scanning Calorimetry

The extrapolated endothermic onset melting and peak melting temperatures observed for Form I of compound 12 were 173.3° C. and 177.2° C., respectively, along with ΔH=97.0 J/g.

We claim:

1. A crystalline polymorphic form of the compound of formula 6

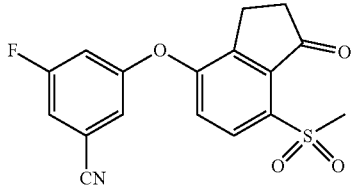

6 which is designated Form I, wherein the crystalline polymorphic form designated Form I has d-spacings determined by x-ray powder diffraction, Cu Kα, of about 11.0, 6.5 and 5.6 angstroms.

2. The crystalline polymorphic form of claim 1, wherein the crystalline polymorphic form has at least two additional d-spacings determined by x-ray powder diffraction, Cu Kα, selected from about 11.4, 4.2, 3.8, and 2.9 angstroms.

3. The crystalline polymorphic form of claim 1, wherein the crystalline polymorphic form has a Differential Scanning Calorimetry (DSC) extrapolated onset melting temperature of about 185.8° C.

4. The crystalline polymorphic form of claim 3, wherein the crystalline polymorphic form has a Differential Scanning Calorimetry (DSC) peak melting temperature of about 187.6° C.

5. A process for preparing the crystalline polymorphic form of claim 1, comprising:
providing a slurry of the compound of formula 6 in isopropyl alcohol; and
isolating the crystalline polymorphic form.

6. A crystalline polymorphic form of the compound of formula 7

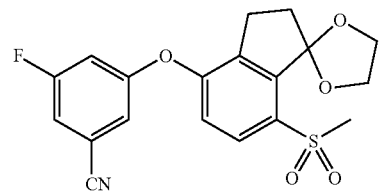

7 which is designated Form I, wherein the crystalline polymorphic form designated Form I has d-spacings determined by powder diffraction, Cu Kα, of about 13.1, 5.7, and 3.9 angstroms.

7. The crystalline polymorphic form of claim 6, wherein the crystalline polymorphic form has at least two additional d-spacings determined by x-ray powder diffraction, Cu Kα, selected from about 6.7, 5.2, 5.1, 4.2, 4.0, or 3.8 angstroms.

8. The crystalline polymorphic form of claim 6, wherein the crystalline polymorphic form has a Differential Scanning Calorimetry (DSC) extrapolated onset melting temperature of about 167.6° C.

9. The crystalline polymorphic form of claim 8, wherein the crystalline polymorphic form has a Differential Scanning Calorimetry (DSC) peak melting temperature of about 169.9° C.

10. A process for preparing the crystalline polymorphic form of claim 6, comprising:
   providing a solution of the compound of formula 7 in isopropyl alcohol;
   allowing the crystalline polymorphic form to precipitate; and
   isolating the precipitated crystalline polymorphic form.

11. A crystalline polymorphic form of the compound of formula 10

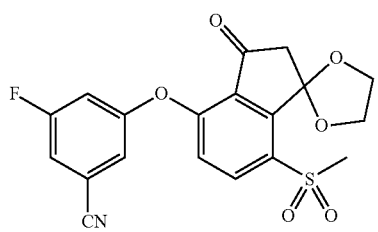

which is designated Form I, wherein the crystalline polymorphic form designated Form I has d-spacings determined by powder diffraction, Cu Kα, of about 13.1, 5.4, and 3.9 angstroms.

12. The crystalline polymorphic form of claim 11, wherein the crystalline polymorphic form has at least two additional d-spacings determined by x-ray powder diffraction, Cu Kα, selected from about 9.1, 6.3, 5.1, 4.1, and 3.7 angstroms.

13. The crystalline polymorphic form of claim 11 or 12, wherein the crystalline polymorphic form has a Differential Scanning Calorimetry (DSC) extrapolated onset melting temperature of about 236.7° C.

14. The crystalline polymorphic form of claim 11, wherein the crystalline polymorphic form has a Differential Scanning Calorimetry (DSC) peak melting temperature of about 238.2° C.

15. A process for preparing the crystalline polymorphic form of claim 11, comprising:
   providing a solution of the compound of formula 10 in isopropyl alcohol and water;
   allowing the crystalline polymorphic form to precipitate; and
   isolating the precipitated crystalline polymorphic form.

16. A crystalline polymorphic form of the compound of formula 11

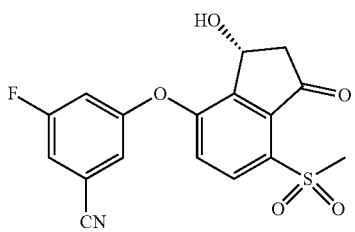

which is designated Form I, wherein the crystalline polymorphic form designated Form I has d-spacings determined by powder diffraction, Cu Kα, of about 12.8, 6.0, and 4.2 angstroms.

17. The crystalline polymorphic form of claim 16, wherein the crystalline polymorphic form has at least two additional d-spacings determined by x-ray powder diffraction, Cu Kα, selected from about 9.6, 7.8, 4.4, 3.8, and 3.7 angstroms.

18. The crystalline polymorphic form of claim 16 or 17 wherein the crystalline polymorphic form has a Differential Scanning Calorimetry (DSC) extrapolated onset melting temperature of about 180.9° C.

19. The crystalline polymorphic form of claim 16, wherein the crystalline polymorphic form has a Differential Scanning Calorimetry (DSC) peak melting temperature of about 182.9° C.

20. A process for preparing the crystalline polymorphic form of claim 16, comprising:
   providing a slurry of the compound of formula 11 in acetonitrile and water; and
   isolating the crystalline polymorphic form.

21. A crystalline polymorphic form of the compound of formula 12

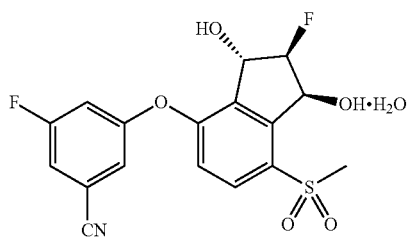

which is designated Hydrate Form I, wherein the crystalline polymorphic form designated Hydrate Form I has d-spacings determined by powder diffraction, Cu Kα, of about 5.5, 5.3, 4.0, and 3.9 angstroms.

22. The crystalline polymorphic form of claim 21, wherein the crystalline polymorphic form has at least two additional d-spacings determined by x-ray powder diffraction, Cu Kα, selected from about 4.7, 3.7, 3.6, 3.4 and 3.1 angstroms.

23. A process for preparing the crystalline polymorphic form of claim 21, comprising: providing a slurry of the compound of formula 12 in acetonitrile and water; allowing the crystalline polymorphic form to precipitate; and isolating the precipitated crystalline polymorphic form.

24. A crystalline polymorphic form of the compound of formula 12

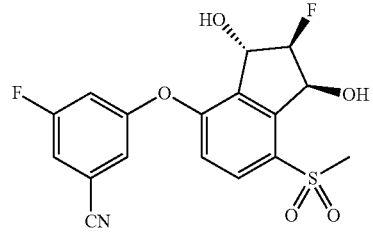

which is designated Form I, wherein the crystalline polymorphic form designated Form I has d-spacings determined by powder diffraction, Cu Kα, of about 11.4, 6.0, 5.8, and 4.4 angstroms.

25. The crystalline polymorphic form of claim 24, wherein the crystalline polymorphic form has at least two additional d-spacings determined by x-ray powder diffraction, Cu Kα, selected from about 4.1, 3.9, 3.8, 3.7, and 3.6 angstroms.

26. The crystalline polymorphic form of claim 24 or 25, wherein the crystalline polymorphic form has a Differential Scanning Calorimetry (DSC) extrapolated onset melting temperature of about 173.3° C.

27. The crystalline polymorphic form of claim 24, wherein the crystalline polymorphic form has a Differential Scanning Calorimetry (DSC) peak melting temperature of about 177.2° C.

28. A process for preparing the crystalline polymorphic form of claim 24, comprising: providing a solution of the compound of formula 12 in n-heptane and ethyl acetate; allowing the crystalline polymorphic form to precipitate; and isolating the precipitated crystalline polymorphic form.

* * * * *